United States Patent [19]

Rudnick et al.

[11] Patent Number: 4,877,866
[45] Date of Patent: Oct. 31, 1989

[54] METHOD OF PRODUCING A VIRUS SAFE, STORAGE-STABLE, AND INTRAVENOUSLY TOLERABLE IMMUNOGLOBULIN-G PREPARATION

[75] Inventors: Dieter Rudnick, Rödermark; Norbert Kothe, Kronberg/Ts.; Herbert Dichtelmüller, Sulzbach/Ts.; Detlef Piechaczek, Münster; Wolfgang Stephan, Dreieich; Hans Schleussner, Frankfurt am Main, all of Fed. Rep. of Germany

[73] Assignee: Biotest Pharma GmbH, Frankfurt, Fed. Rep. of Germany

[21] Appl. No.: 122,092

[22] Filed: Nov. 18, 1987

[30] Foreign Application Priority Data

Nov. 27, 1986 [DE] Fed. Rep. of Germany ....... 3640513

[51] Int. Cl.$^4$ ..................... A61K 39/395; A61K 41/00
[52] U.S. Cl. ................. 530/387; 204/157.68; 422/24; 424/85.8; 424/101
[58] Field of Search .................. 530/387; 424/85, 101, 424/85.8; 514/21; 422/24; 204/157-168

[56] References Cited

U.S. PATENT DOCUMENTS

| | | | |
|---|---|---|---|
| 2,710,293 | 6/1955 | Gerlough | 530/387 X |
| 2,710,294 | 6/1955 | Gerlough | 530/387 X |
| 3,916,026 | 10/1975 | Stephan | 514/21 |
| 3,984,539 | 10/1976 | Khouw et al. | 530/387 X |
| 4,136,094 | 1/1979 | Condie | 530/387 X |
| 4,305,870 | 12/1981 | Liu et al. | 530/387 |
| 4,318,902 | 3/1982 | Stephan | 424/85 |
| 4,322,403 | 3/1982 | Bünnig | 424/101 X |
| 4,388,232 | 6/1983 | Eibl et al. | 530/387 X |
| 4,482,483 | 11/1984 | Curry et al. | 530/387 X |
| 4,639,513 | 1/1987 | Hou et al. | 530/387 |

Primary Examiner—Howard E. Schain
Attorney, Agent, or Firm—Sprung Horn Kramer & Woods

[57] ABSTRACT

A method of producing a virus-safe, storage-stable, and intravenously tolerable immunoglobulin-G preparation. The object is to make the method appropriate for industrial-scale production and economical by means of the enrichment and multistage purification of a plasma that has had the coagulation factors removed from it or of a plasma fraction or serum fraction that contains immunoglobulin G accompanied by treatment with ion exchangers and by ultrafiltration. The precipitant is eliminated, by means of diafiltration or gelfiltration, either from the plasma that has had the coagulation factors removed from it or from the plasma fraction that contains the immunoglobulin G, and the desired ion composition is established. The resulting protein solution is subjected to fractionation over an ion exchanger to separate the immunoglobulin G. The proteolytic enzymes in the resulting immunoglobulin-G solution are removed by means of affinity chromatography over a dye linked sorbent and/or are ihibited by the addition of antithrombin III. The accordingly stabilized immunoglobulin-G solution is treated, at a protein concentration of 20 to 60 g/l and a pH 6.0 to 8.0, with 0.03 to 0.07% of β-propiolactone, diluted to a protein concentration of 5 to 20 g/l and subjected to ultraviolet radiation. The accordingly sterilized dilute immunoglobulin-G solution is again diafiltered or gelfiltered to remove lower molecular-weight substances. The accordingly stabilized and sterilized solution is adjusted to the desired protein content of 2 to 16% and filtered sterile.

13 Claims, No Drawings

METHOD OF PRODUCING A VIRUS SAFE, STORAGE-STABLE, AND INTRAVENOUSLY TOLERABLE IMMUNOGLOBULIN-G PREPARATION

The invention concerns the method of producing a virus-safe, storage-stable, and intravenously tolerable immunoglobulin-G preparation recited in the claims.

Immunoglobulin preparations obtained by fractionation from human plasma have been used for more than 30 years for the treatment of inherited and acquired immune-deficiency conditions. Those obtained by fractionation with cold ethyl alcohol (Cohn fractionation), however, can be administered only intramuscularly because intravenous administration leads to extremely severe side reactions. Since intravenously administered immunoglobulin preparations are very effective, methods of producing intravenously compatible preparations from alcohol-fractionated immunoglobulin have already been described. In these methods, which are reviewed in Krankenhauspharmazie 6, 5, 226-31 (1985), the immunoglobulin molecule is either enzymatically split, with plasmin for example, or chemically modified, with $\beta$-propiolactone for example, or an attempt is made either to prevent the formation of anticomplementary aggregates by means of specific precipitation, absorption, and chromatographic techniques and by adding stabilizers or to remove the aggregates and produce a non-modified immunoglobulin G.

Neither enzymatically split nor chemically modified immunoglobulins G can carry out all the functions of the natural immunoglobulin, however, because the aforesaid methods change the properties of the protein—decreasing half-time and effectiveness or decelerating the initiation of action.

These drawbacks have led to the development of alternative immunoglobulin-fractionation methods. Precipitation with such colloids as polyethylene glycol (PEG) or polyethylene glycol plus hetastarch (HES), however, leads to the infusion of any residual colloid, and precipitation with polyethylene glycol is already a known method of viral enrichment. Nor do these fractionation methods eliminate the high anticomplementary activity.

Baumstark et al (Archives of Biochemistry and Biophysics 108, 514-22 [1984]) describe a method of isolating immunoglobulin G from human plasma that employs ion exchangers, especially anion exchangers such as DEAE Sephadex, for discontinuous separation. Suomela et al. (in Curling, Separation of Plasma Proteins, Pharmacia Fine Chemicals, 1983, pp. 127-30) describe a method that among other stages employs gel filtration, chromatography over an anion exchanger, and chromatography over a cation exchanger to isolate immunoglobulin G from plasma.

Friedli and Kistler (in Curling, Methods of Plasma Protein Fractionation, Academic Press, 1980, pp. 203-10) describe using gel filtration to remove ethyl alcohol and salts from a solution of albumin. Martinache and Henon (op. cit., pp. 223-35) describe using ultrafiltration to purify immunoglobulin-G solutions by removing ethyl alcohol and salts. Suomela (op. cit., pp. 107-16) notes that commercially available immunoglobulin-G preparations are usually not storage-stable because they contain proteolytic enzymes that break down the immunoglobulin-G molecule. Suomela attempted to remove the plasminogen from an immunoglobulin-G preparation obtained through ion-exchanger chromatography over lysine - agarose. He reports, however, that the method was unable to remove all the proteolytic enzymes. Suzuki and Takahashi (Methods in Enzymology 34, 432-35 [1974]) describe obtaining pure prekallikrein from a pseudoglobulin fraction through adsorption on arginine - agarose.

Treating an immunoglobulin fraction with specific adsorbents will not eliminate all the proteinase activity because the fractions may contain, depending on the starting material, various amounts of such enzymes as prekallikrein, kallikrein, plasminogen, plasmin, thrombin, or factor XI.

Furthermore, pathogenic virsus can generally be transmitted with blood, human plasma, or plasma fractions. These viruses include in particular hepatitis viruses B and non-A/non-B and AIDS viruses, which can lead to life-threatening diseases.

It is accordingly absolutely necessary to subject purified plasma-protein fractions to a sterilization process that will adequately inactivate the viruses. This is especially true when the plasma fractions have been obtained from pools of more than 1000 donors.

Methods of sterilizing plasma and some plasma-protein fractions such as those (factors VIII and IX and fibrinogen for instance) employed in coagulation preparations are known. The known methods include heating in solution, in the lyophilized state, and in pressurized steam and sterilization with detergents. German Patent 3 033 932 in particular describes the sterilization of plasma intended as a starting material for the production of coagulation preparation by means of a combination of treatment with $\beta$-propiolactone and with ultraviolet radiation.

Sterilization has always been considered unncessary for immunoglobulin preparations because immunoglobulins obtained by Cohn fractionation were considered virus-safe. The Lancet, pp. 322 and 581-82 (1986), however, describes the transmission of hepatitis viruses B, non-A/non-B, and A and possibly AIDS viruses by immunoglobulin-G preparation. Since the transmission of the viruses non-A/non-B may have something to do with chromatographically purified immunoglobulin, it would seem to be absolutely necessary to be able to sterilize immunoglobulins as well.

Immunoglobulin preparations produced by chromatographic methods are not stable in the liquid state and entail the risk of transmitting viruses. It is impossible to heat-sterilize these preparations because the heat would lead to the formation of aggregates and increase anticomplementary activity. Treatment with such detergents as sorbimacrogololeate involves the very troublesome step of removing the detergents from the preparation. Although reaction with $\beta$-propiolactone does, as demonstrated by Stephan and Dichtelmüller (Arzneim.-Forsch./Drug Res. 33 [II], 9, 1230-31 [1983]), lead to a virus-safe preparation subject to the known conditions, it will also chemically modity the protein.

The object of the invention is to provide an industrial-scale and economical method of producing an unmodified, intact, high-purity, virus-safe, and storage-stable immunoglobulin-G preparation, which will be free of anticomplementary activity and hence intravenously tolerable, by means of the enrichment and multistage purification of a plasma that has had the coagulation factors removed from it or of a plasma fraction or serum fraction that contains immunoglobulin G accompanied by treatment with ion exchangers and by ultrafiltration.

This object is attained in accordance with the invention in that (a) the precipitant is eliminated, by means of diafiltration or gel filtration, either from the plasma that has had the coagulation factors removed from it or from the plasma fraction that contains the immunoglobulin G, and the desired ion composition is established, (b) the resulting protein solution is subjected to fractionation over an ion exchanger to separate the immunoglobulin G, (c) the proteolytic enzymes in the resulting immunoglobulin-G solution are removed by means of affinity chromatography over a sorbent that is linked to a dye and/or are inhibited by the addition of antithrombin III, (d) the accordingly stabilized immunoglobulin-G solution is treated, at a protein concentration of 20 to 60 g/l and a pH 6.0 to 8.0, with 0.03 to 0.07% of $\beta$-propiolactone, diluted to a protein concentration of 5 to 20 g/l, and subjected to ultraviolet radiation.

(e) the accordingly sterilized dilute immunoglobulin-G solution is again diafiltered or gel filtered to remove lower molecular-weight substances, and (f) the accordingly stabilized and sterilized solution is adjusted to the desired protein content of 2 to 16% and filtered sterile.

The method in accordance with the invention can be carried out with either human or animal starting materials.

Any of a plasma has had the coagulation factors removed from it, a serum, a $\gamma$-globulin (Cohn's paste II or II/III) that has been isolated by Cohn fractionation and occurs in large quantities during the industrial-scale production of human albumin, or even a raw $\gamma$-globulin fraction that has been isolated by salt precipitation (with ammonium sulfate for example), can be employed. The starting materials can be harvested from either normal donor pools or from specially selected donors with high antibody titers against viral and bacterial antigens.

A preferred starting material for the method in accordance with the invention is either a plasma that has had the coagulation factors removed from it or a Cohn's paste II or II/III.

The coagulation factors are themselves highly valuable therapeutically. Furthermore, they interfere with further plasma fractionation. Separating them from the plasma is accordingly known. Thus, for example, a cryoprecipitate obtained from a thawing process is employed as a starting material for the production of factor-VIII concentrates, and factors II, VII, IX, and X (PPSB complex) are isolated by adsorption onto an anion exchanger, purified, and also employed therapeutically.

The preferred starting material is accordingly obtained for the method in accordance with the invention by preparing plasma by plasmapheresis in accordance with standard blood-collection practice, thawing it out at $+4°$ C., and centrifuging the cryoprecipitate out. The coagulation factors are removed from the PPSB complex by adsorption onto an anion exchanger, a cross-linked dextran substituted with diethylamino groups for example. The resulting plasma can preferably be treated with ethyl alcohol to precipitate the remaining fibrinogen. Although this step is not absolutely necessary, it does avoid contamination of the column materials during the subsequent chromatographic steps. The conditions for this step, specifically an ethyl-alcohol concentration of 8 to 11% of pH of 4.5 to 6.5, are selected to prevent formation of aggregates in the immunoglobulin fraction.

A plasma treated in this way will have the following composition:

| Protein | 40–55 g/l |
|---|---|
| Immunoglobulin-G | 5.0–7.5 g/l |
| Alcohol | 8–11% |
| $\alpha_1$ Globulin | 2.5–3.5% |
| $\alpha_2$ Globulin | 7.0–9.0% |
| $\beta$ Globulin | 7.0–9.0% |
| $\gamma$ Globulin | 11–15% |
| Albumin | 62–68% |
| (electrophoresis on cellulose-acetate film). | |

This coagulation-factor free plasma, or even the enriched immunoglobulin factor, due to the preliminary treatment, will contain considerable amount of (ethyl) alcohol or other precipitants. Furthermore, its ionic environment will be dictated either by the natural composition or plasma or by the preliminary treatment.

It is necessary for purposes of further processing to remove the alcohol or other precipitant and establish a definite ionic environment. This is the next step. This can be done by diafiltration with a 5- to 10-fold replacement volume. Ultrafiltration membranes with an exclusion range of 10 to 1000 kD are employed, either flat or hollow-fiber. The desired protein concentration (20–30 g/l) is established at the end of the process.

Gel filtration is preferably employed at this stage. Gel filtration is based on the principle of employing porous gels that decelerate lower molecular-weight substances like alcohol and salts and allow higher molecular-weight materials like plasma proteins to pass through the gel matrix without interacting with it. This principle is exploited to separate lower molecular-weight substances out while simultaneously establishing the desired ion composition in accordance with the composition of the mobile phase. Appropriate materials for gel filtration are those with an exclusion range of 2 to 10 kD, those based for example on cross-linked dextran, copolymers of N-acryloyl-2-amino-2-hydroxymethyl-1,3-propandiol, or cellulose, such as Sephadex G-25, Trisacryl GF 05, or Cellufine GH 25.

Before receiving the protein solution, the gel is equilibrated in a chromatography column with the desired buffer system. Buffer systems with a molarity of 0.01 to 0.5 and a pH of 4.5 to 8.5, depending on whether the further processing will be carried out on anion or cation exchangers, are appropriate.

The resulting protein solution will be free of alcohol and interfering salts and will be composed of Protein: 20–30 g/l
Immunoglobulin G: 2.5–3.7 g/l
$\alpha_1$ Globulin: 2.5–3.5%
$\alpha_2$ Globulin: 7.0–9.0%
$\beta$ Globulin: 7.0–9.0%
Albumin: 62–68%
$\gamma$ Globulin: 11–15%
(electrophoresis on cellulose-acetate film).

This protein solution is fractionated over ion exchangers to separate the immunoglobulin G from the other proteins. When cation exchangers (e.g. agarose substituted with sulfopropyl or carboxymethyl groups or copolymers of N-acryloyl-2-amino-2-hydroxymethyl-1,3-propandiol, such as S-Sepharose, SP-Trisacryl, or CM-Sepharose) are employed, the conditions are selected (buffer 0.01–0.05 molar and pH 4.5–6.5) to ensure that the the immunoglobulin-G fraction will attach to the exchanger matrix, whereas all the other plasma proteins will pass through it unimpeded along with the mobile phase. The attached immunoglobulin G is then eluted with a buffer with a high salt concentration—0.5 to 1.5 molar.

The yield of immunoglobulin G from this procedure is approximately 60%, and the immunoglobulin-G fraction will contain small amounts of immunoglobulin A and immunoglobulin M.

The plasma is accordingly preferably fractionated over anion exchangers (e.g. agarose substituted with diethylaminoethyl groups, copolymers of N-acryloyl-2-amino-2-hydroxymethyl-1,3-propandiol, cellulose, or silicic acid, or a polymer of monomers containing methacrylamide and N-methylenebismethacrylamide substituted with quaternary aminoethyl groups, such as DEAE-Sepharose, DEAE-Trisacryl, DEAE-cellulose, DEAE-Spherosil, QMA-Accel, or QAM-Eupergit) to harvest the immunoglobulin-G fraction. The buffer environment is in this case selected (0.01–0.05 molar, pH 6.5–8.5) to ensure that all the plasma proteins will attach to the anion-exchanger matrix, whereas the immunoglobulin-G fraction can be obtained as a pure fraction, without interacting with the gel bed.

This procedure leads to a yield of approximately 90% immunoglobulin-G fraction, consisting of up to 100% γ globulin (electrophoresis on cellulose-acetate film) with no contamination in the form of immunoglobulin A, immunoglobulin M, or other plasma proteins. This high-purity and dilute immunoglobulin-G fraction is diafiltered to remove buffer substances as against physiologically compatible salt solutions and concentrated by ultrafiltration to establish the desired protein concentration. Appropriate for this purpose are flat or hollow-fiber ultrafiltration membranes with an exclusion range of 10 to 100 kD.

The immunoglobulin-G solution, which has been concentrated in this way or in other known ways—by precipitation, freeze drying, or spray drying followed by solubilization or by adsorption over cation exchangers followed by elution—to a protein content of approximately 50 to 110 g/l, is, however, still not storage-stable because decomposition products will still appear after a while. It has been demonstrated, using the enzyme substrate S 22 88 (Kabi), that the immunoglobulin-G fraction still contains considerable proteolytic activity—up to 10 000 U/l. It has been possible, with such specific enzyme substrates as plasmin, plasminogen, thrombin, and prekallikrein substrates, to demonstrate traces of these enzymes. Current measures for removing the enzymes—such as adsorption onto barium sulfate, white clay, agar, colloidal silicic acid, active charcoal, affinity exchangers, or cation or anion exchangers or such as adding aprotinin, amino acids, and such enzyme inhibitors as fluorine compounds—did not result in satisfactory separation or inhibition.

The proteolytic enzymes are accordingly separated in accordance with the invention by affinity chromatography over a sorbent in association with a dye, chromium blue (Ciba) for example, coupled to agarose, cellulose, or a copolymer of N-acryloyl-2-amino-2-hydroxymethyl-1-1,3-propandiol, such as Sepharose, cellulose, or Trisacryl, or inhibited by adding antithrombin III.

The effectiveness of the affinity chromatography in accordance with the invention will be evident from Table I. The batches 1 through 5 listed therein were obtained by the procedure described with reference to Example 2 hereinbelow.

TABLE I

| Proteolytic activity of immunoglobulin-G preparations subsequent to storage for 4 weeks at 37° C. | | |
|---|---|---|
| Batch | Proteolytic activity U/l | Degradation product (HPLC) |
| 1 | 13 | <1% |
| 2 | 7 | <1% |
| 3 | 17 | <1% |
| 4 | 11 | <1% |
| 5 | 10 | <1% |

The effectiveness of adding purified antithrombin III in accordance with the invention to inhibit the proteolytic enzymes will be evident from Table II. The batches 1 through 4 listed therein were obtained by the procedure described with reference to Example 1 hereinbelow.

TABLE II

| Proteolytic activity of immunoglobulin-G preparations subsequent to storage for 4 weeks at 37° C. | | |
|---|---|---|
| Batch | Proteolytic activity U/l | Degradation product (HPLC) |
| 1 | 7 | <1% |
| 2 | 11 | <1% |
| 3 | 4 | <1% |
| 4 | 10 | <1% |

To obtain a storage-stable solution of immunoglobulin G it is necessary to add 0.5 to 3 U/ml of antithrombin III.

Once it has been purified and stabilized as described, the immunoglobulin-G fraction might still be contaminated with such pathogenic viruses as hepatitis B, hepatitis non-A/non-B, hepatitis A, or HTLV-III/LAV.

Sterilization is accordingly carried out in accordance with the invention in order to obtain a virsus-safe immunoglobulin-G preparation. Although EPA 0 102 731 describes using ion exchangers to reduce HBsAg, tests still indicate that this decrease is not enough to obtain a really virus-safe product.

If $4.6 \times 10^{10}$ κ model viruses (bacteriophages) or HBsAg, representing hepatitis viruses B, are added to a plasma prepared in accordance with the invention before fractionation over an ion exchanger, $8.3 \times 10^3$ viruses will remain in the isolated immunoglobulin-G fraction. Table III lists the corresponding results.

TABLE III

| Distribution of viruses during the chromatographic purification of immunoglobulin-G (in a DEAE-Trisacryl column) | | | | |
|---|---|---|---|---|
| Treatment | HBsAg (mg/ml) | Sendai virus | f-2 (titer × volume) | κ |
| Before chromatography | 7.96 | $1.0 \times 10^2$ | $2.2 \times 10^{10}$ | $4.6 \times 10^{10}$ |
| After chromatography | 0.017 | negative | $8.3 \times 10^3$ | $8.3 \times 10^3$ |
| Titer reduction | 99.79% | >2.0 log$_{10}$ | 6.4 log$_{10}$ | 6.7 log$_{10}$ |
| Chromatography eluate | 8.57 | $5.0 \times 10^2$ | $1.8 \times 10^8$ | $2.4 \times 10^9$ |

This decrease is not enough to ensure a virus-safe immunoglobulin-G preparation. The method in accordance with the invention accordingly includes additional sterilization, employing a combination of β-propiolactone and ultraviolet radiation.

The purified immunoglobulin-G fraction is treated at a protein concentration of 20 to 60 g/l with 0.03 to 0.07 and preferably with 0.05% β-propiolactone at a pH of 6.0 to 8.0 and preferably 7.2. Subsequent to a reaction time of 3 to 24 hours the immunoglobulin soltuion is diluted to a protein content of 5 to 20 g/l and subjected to ultraviolet radiation in a rotary flowthrough apparatus. The accordingly sterilized solution is then adjusted by known procedures to 4 to 12% protein. As will be evident from Table IV, the method in accordance with the invention adequately inactivates the model viruses.

TABLE IV

Inactivation of bacteria and viruses in chromatographically purified immunoglobulin-G by means of β-propiolactone (BPL) and ultraviolet radiation (UV)

| Treatment | Φ −x 174 | Φ −e | κ |
|---|---|---|---|
| Before BPL | $2.9 \times 10^7$ | $3.8 \times 10^7$ | $1.3 \times 10^9$ |
| Titer reduction ($\log_{10}$) after BPL | 6.05 | 5.2 | 0.85 |
| Titer reduction ($\log_{10}$) after BPL + UV | >7.5 | >7.4 | 8.3 |

The virus inactivation of at least 7.5 $\log_{10}$ (titer reduction) represents adequate viral safety in relation to hepatitis viruses B and non-A/non-B and AIDS viruses.

Whereas the known virus-inactivation action of β-propiolactone leads to a demonstrable chemical modification of the immunoglobulins, the method in accordance with the invention employs a definitely lower β-propiolactone concentration, in combination with ultraviolet radiation, than does the known method and gives surprising results in effective virus inactivation without demonstrably altering the immunoglobulins or having a detrimental effect on their activity. Table V illustrates the situation.

TABLE V

Effects of sterilization with β-propiolactone and ultraviolet radiation on chromatographically sterilized immunoglobulin-G

| Sample state | Reciprocal antibody activity (PHA) | | | | KBR (μl/mg) | Degree of modification (%) | Polymer content (%) |
|---|---|---|---|---|---|---|---|
| | E. coli | Ps. aer. | Klebs. | Staph. | | | |
| Before sterilization | 40 (12) | 80 (12) | 160 (19) | 20 (14) | >135 | | not demonstrable |
| After sterilization | 40 (12) | 80 (15) | 160 (19) | 10 (8) | 15 | not demonstrable | <1.0 |

The immunoglobulin-G preparation produced in accordance with the invention is surprisingly outstanding for its combination of the following properties:

It is pure, consisting of approximately 100% γ globulin (by electrophoresis on cellulose-acetate film).

It is free of immunoglobulins A and M.

The yield is up to 90% immunoglobulin G.

It contains all the immunoglobulin-G subclasses.

It contains no higher molecular-weight aggregates, accordingly exhibits a low non-specific anticomplementary activity, and is accordingly intravenously tolerable.

The immunoglobulin solution is sterilized, virus-free, natural, and unmodified.

It contains such low levels of active proteases that no degradation products can be demonstrated, and is storage-stable.

These properties satisfy all the requisites for an immunoglobulin preparation.

The invention will now be specified with reference to the following examples.

EXAMPLE 1

A. A pool of fresh-frozen human plasma was thawed at +4° C. and the residual precipitate (cryoprecipitate) centrifuged out. The clear residue was treated with swollen and equilibrated ion exchanger (DEAE Sephadex) to separate it from the factors of the PPSB complex and stirred for 1 hour at room temperature. The gel was removed over a filter and the residue treated with 9% ethyl alcohol by volume at a pH of 5.3. The batch was allowed to stand for 3 hours at -3° C. and the precipitate, mainly fibrinogen, centrifuged out. The batch was then filtered sterile.

B. The resulting plasma, which was free of coagulation factors, was gel filtered, to remove the alcohol and adjust an ionic environment to 0.022 M of (tris[hydroxymethyl]aminomethane) plus hydrochloric acid (TRIS +HCl) pH 7.5 in a column that had been equilibrated with the same combination at the same pH and packed with 22 l of Sephadex G-25. It took 12 gel-filtration cycles to completely re-buffer the plasma. The collected fractions, with a protein content of 22 g/l were filtered sterile.

C. The immunoglobulin G was separated from the accordingly re-buffered plasma by means of anion-exchanger chromatography, using a 10-l column packed with DEAE-Trisacryl LS and equilibrated with 0.022 M TRIS+HCl at a pH of 7.5. The re-buffed plasma was fractionated over the anion exchanger in 12-l portions, attaching all the plasma proteins except immunoglobulin G to the exchanger. It took 6 cycles to process all the plasma. Each attached plama protein was eluted with 0.22 M of TRIS+HCl and 0.6 M of NaCl a pH of 7.5 and collected for other uses.

D. The combination immunoglobulin G fractions, which had a protein content of 1.5 g/l and a volume of 120 l, were concentrated to a protein content of g/l by means of an ultrafiltration system (exclusion limit of 10 kD. At a pH of 7.2 the solution was adjusted to a physiological environment with solid sodium chloride and treated with 1.5 U/ml of antithrombin III to inhibit any proteolytic enzymes.

E. The immunoglobulin G solution from state D was treated at a pH of 7.2 with β-propiolactone (0.5 ml per l of solution), with the pH being maintained constant over the reaction time of 12 hours. The solution was then diluted with physiological sodium chloride solution to a protein content of 10 g/l and subjected to ultraviolet radiation in a rotary apparatus with a flow rate of 20 l/h and an intensity of 1 mW/cm$^2$×min.

F. The accordingly sterilized immunoglobulin-G solution was then gel filtered for 4 cycles in a column packed with 22 l of Sephadex G-25 and equilibrated with a semiphysiological sodium chloride solution to remove the TRIS+HCl buffer. The solution was concentrated in an ultrafiltration apparatus (exclusion limit of 10 kD) to a protein content of 50 g/l, 0.150 moles of glycine were added, and the batch was filtered sterile.

The resulting immunoglobulin-G solution had the following properties:

| | |
|---|---|
| Yield | 72% |
| Protein | 58.8 g/l |
| Immunoglobulin-G | 53.5 g/l |
| γ Globulins | 100% (electrophoresis on cellulose-acetate film) |
| Complement fixation | 11 μl/mg of protein |
| Proteolytic activity | 7 U/l |
| Gel filtration (HPLC) | 95% monomer |
| | 5% dimer |
| | −% polymer |
| | −% degradation product |
| Modification | not detectable. |

EXAMPLE 2

The identical procedure described with reference to Example 1 was followed from step A to step C.

D. The immunoglobulin-G fraction with a protein content of 1.5 g/l was adjusted to a physiological saline concentration with solid sodium chloride. A chromatography column was packed with 3 l of Ciba chromium blue coupled with Trisacryl LS and equilibrated with 0.022 M of TRIS+HCl and 0.15 M of sodium chloride at a pH of 7.5. 20 l of the purified, isotonic, and dilute immunoglobulin-G solution were pumped over the gel bed at a flow rate of 6 l/h. The immunoglobulin-G solution, now free of proteolytic enzymes, was concentrated to 40 g/l in an ultrafiltration apparatus.

The rest of the procedure was identical to the steps E and F described with reference to Example 1.

The resulting immunoglobulin-G solution had the following properties.

| | |
|---|---|
| Yield | 62% |
| Protein | 53.5 g/l |
| Immunoglobulin-G | 51.5 g/l |
| γ Globulins | 99.1% (electrophoresis on cellulose-acetate film) |
| Complement fixation | 15 μg/mg of protein |
| Proteolitic activity | 18 U/l |
| Gel filtration (HPLC) | 93.4% monomer |
| | 5.89% dimer |
| | 0.66% polymer |
| | −% degradation product |
| Modification | not detectable. |

EXAMPLE 3

The procedure described with reference to step A in Example 1 was repeated, but without the treatment with ethyl alcohol, with another pool of 50 l of human plasma. The plasma, free of coagulation factors, was filtered free of ion-exchanger gel and immediately processed as described in step B (gel filtration), adjusting the ionic environment with 0.022 M of TRIS+HCl at a pH of 7.5. Steps B through F of Example 1 or 2 were then followed.

The resulting immunoglobulin-G solution had the following properties:

| | |
|---|---|
| Yield | 70% |
| Protein | 52.4 g/l |
| Immunoglobulin-G | 51.8 g/l |
| γ Globulins | ~ 100% (electrophoresis on cellulose-acetate film) |
| Complement fixation | 11 μl/mg of protein |
| Gel filtration (HPLC) | 85.8% monomer |
| | 14.1% dimer |
| | −% polymer |
| | −% degradation product |
| Modification | not detectable. |

EXAMPLE 4

A. 1 kg of crude γ-globulin paste (Paste II/III) obtained from human plasma by Cohn's alcohol-fractionation method was dissolved in 11 l of 0.15 M sodium-dihydrogen phosphate buffer at a pH of 5.2. The protein content of the solution was 20 g/l. It was centrifuged and filtered to remove the insoluble constituents.

B. The resulting solution was gel filtered as described in Example 1, step B to remove the alcohol and adjust the ionic environment to 0.022 M of TRIS+HCl at a pH of 7.5.

The solution obtained in step B, which had a protein content of 15 g/l, was then processed as described with reference to steps C through F in Examples 1 and 2.

The resulting immunoglobulin-G solution had the following properties:

| | |
|---|---|
| Yield | 56% |
| Protein | 51.2 g/l |
| Immunoglobulin-G | 49.7 g/l |
| γ Globulins | 98% (electrophoresis on cellulose-acetate film) |
| Complement fixation | 20 μl/mg of protein |
| Gel filtration (HPLC) | 93.1% monomer |
| | 6.9% dimer |
| | −% polymer |
| | −% degradation product |
| Modification | not detectable. |

EXAMPLE 5

The procedure was similar to that described with reference to Example 1, steps A through F, except that Sepharose Q was employed in step C instead of DEAE-Trisacryl.

The resulting immunoglobulin-G solution had the following properties:

| | |
|---|---|
| Yield | 58.5% |
| Protein | 48.7 g/l |
| Immunoglobulin-G | 46.2 g/l |
| γ Globulins | 98.9% (electrophoresis on cellulose-acetate film) |
| Complement fixation | 19 μl/mg of protein |
| Proteolitic activity | 17 U/l |
| Gel filtration (HPLC) | 93.5% monomer |
| | 6.5% dimer |
| | −% polymer |
| | −% degradation product |
| Modification | not detectable. |

EXAMPLE 6

The procedure of Example 1, steps A through F, was followed except that DEAE-Spherosil was employed instead of DEAE-Trisacryl LS in step C.

The resulting immunoglobulin-G solution had the following properties:

| | |
|---|---|
| Yield | 70% |
| Protein | 49.5 g/l |
| Immunoglobulin-G | 53.5 g/l |
| γ Globulins | 100% (electrophoresis on cellulose-acetate film) |
| Complement fixation | 15 μl/mg of protein |
| Proteolytic activity | 9 U/l |
| Gel filtration (HPLC) | 94.5% monomer |
| | 5.5% dimer |
| | —% polymer |
| | —% degradation product |
| Modification | not detectable. |

EXAMPLE 7

The procedure of Example 1, steps A through F, was followed except that Trisacryl GF 0.5 was employed in step B instead of Sephadex G-25 to remove the alcohol and re-buffer the solution.

The resulting immunoglobulin-G solution had the following properties:

| | |
|---|---|
| Yield | 70% |
| Protein | 51.5 g/l |
| Immunoglobulin-G | 50.2 g/l |
| γ Globulins | ~100% (electrophoresis on cellulose-acetate film) |
| Complement fixation | 13 μl/mg of protein |
| Proteolytic activity | 18 U/l |
| Gel filtration (HPLC) | 95% monomer |
| | 5% dimer |
| | —% polymer |
| | —% degradation product |
| Modification | not detectable. |

EXAMPLE 8

A. This step was identical to the step A in Example 1.

B. The solution obtained in step A was gel filtered over Sephadex G25 that had been equilibrated with 0.025 M of sodium acetate at a pH of 5.8 to remove the alcohol and establish the ionic environment. The collected fractions, with a protein content of 22 g/l, were filtered sterile.

C. A chromatography column packed with 1 l of SP-Trisacryl LS was equilibrated with a 0.025 M sodium acetate buffer at a pH of 5.8, and the re-buffered plasma obtained in step B was chromatographed for 5 cycles of 19 l each. The immunoglobulin-G fraction that attached to the cation exchanger was eluted with 0.025 M of sodium acetate and with 0.6 M of sodium chloride at a pH of 7.5.

D. The collected immunoglobulin-G fractions were concentrated to a protein content of 40 g/l in an ultrafiltration apparatus (exclusion limit of 10 kD) and diafiltered through diatomaceous earth against isotonic saline solution.

The resulting solution was either treated with antithrombin III as described in Example 1 or subjected to affinity chromatography over Ciba chromium blue coupled to Trisacryl LS as described in Example 2. Further processing was identical to steps E and F of Example 1.

The resulting immunoglobulin-G solution had the following properties:

| | |
|---|---|
| Yield | 55% |
| Protein | 52.3 g/l |
| Immunoglobulin-G | 50.3 g/l |
| Immunoglobulin-A | 0.8 g/l |
| Immunoglobulin-M | 0.6 g/l |
| γ Globulins | 100% (electrophoresis on cellulose-acetate film) |
| Complement fixation | 12 μl/mg of protein |
| Gel filtration (HPLC) | 91.5% monomer |
| | 7% dimer |
| | 1.5% polymer |
| | —% degradation product |
| Modification | not detectable. |

It will be understood that the specification and examples are illustrative but not limitative of the present invention and that other embodiments within the spirit and scope of the invention will suggest themselves to those skilled in the art.

What is claimed is:

1. A method of producing a virus-safe, storage-stable, and intravenously tolerable immunoglobulin-G preparation from a plasma that has had the coagulation factors removed from it or of a plasma fraction or serum fraction that contains immunoglobulin G, comprising
   (a) diafiltering or gel filtering either the plasma that has had the coagulation factors removed from it or the plasma or serum fraction that contains the immunoglobulin G to eliminate any precipitant, and establishing an ion composition sufficient for subsequent fractionation,
   (b) subjecting the resulting protein solution from (a) to fractionation over an ion exchanger to separate the immunoglobulin G,
   (c) removing the proteolytic enzymes in the resulting immunoglobulin-G solution of (b) by means of affinity chromatography over a dye linked sorbent and/or inhibiting such enzymes by the addition of antithrombin III,
   (d) treating the accordingly stabilized immunoglobulin-G solution of (c), at a protein concentration of 20 to 60 g/l and a pH of 6.0 to 8.0, with 0.03 to 0.07% of β-propiolactone, diluting it to a protein concentration of 5 to 20 g/l, and subjecting it to ultraviolet radiation,
   (e) again diafiltering the accordingly sterilized dilute immunoglobulin-G solution or gel filtration to remove lower molecular-weight substances, and
   (f) adjusting the accordingly stabilized and sterilized solution to the desired protein content of 2 to 16%, and conducting sterile filtering.

2. The method according to claim 1, wherein step (a) comprises diafiltration with a 5- to 10-fold replacement volume over a membrane with an exclusion range of 10 to 100 kD.

3. The method according to claim 2, wherein step (a) comprises gel filtration over a material with an exclusion range of 2 to 10 kD, employing a buffer system with a molarity of 0.01 to 0.05 and a pH of 4.5 to 8.5 for replacement or equilibration.

4. The method according to claim 3, wherein the filtration gel is a cross-linked dextran gel, a gel based on a copolymer of N-acryloyl-2-amino-2-hydroxymethyl-1,3-propandiol, or a cellulose gel.

5. The method according to claim 4, wherein the filtration gel is Sephadex G-25, Trisacryl GF-05, or Cellufine GH-25.

6. The method according to claim 3, wherein the gel is equilibrated during step (a) with a buffer system with a pH of 6.5 to 8.5, and the fractionation of step (b) is carried out with an anion exchanger that is also equilibrated with a molarity of 0.01 to 0.05 and a pH of 6.5 to 8.5.

7. The method according to claim 6, wherein the anion exchanger is DEAE-Sepharose, DEAE-Trisacryl, DEAE-Cellulose, QAM-Eupergit, or QMA-Accel.

8. The method according to claim 1, wherein 0.1 to 5 U of antithrombin III per ml are added during step (c).

9. The method according to claim 1, wherein step (c) includes affinity chromatography carried out over a sorbent coupled with chromium blue.

10. The method according to claim 9, wherein affinity chromatography is carried out the Trisacryl coupled with chromium blue.

11. The method according to claim 1, wherein the ultraviolet radiation in step (d) is carried out at an intensity of about 1 $mW/cm^{2x}min$.

12. The method according to claim 1, wherein the starting material for step (a) is a plasma from which (i) the cryoprecipitate has been removed and (ii) the coagulation factors in the PPSB complex has been separated by adsorption onto an anion exchanger.

13. The method according to claim 12, wherein (iii) the residual fibrinogen has been removed from the plasma by precipitation with ethyl alcohol.

* * * * *